(12) United States Patent
Pratap et al.

(10) Patent No.: US 6,896,901 B2
(45) Date of Patent: May 24, 2005

(54) METHOD OF TREATING A COGNITIVE MEMORY DYSFUNCTION USING GUGULIPID

(75) Inventors: Ram Pratap, Lucknow (IN); Raghwendra Pal, Lucknow (IN); Satyawan Singh, Lucknow (IN); Girja Shankar, Lucknow (IN); Chandeshwar Nath, Lucknow (IN); Hemant Kumar Singh, Lucknow (IN); Depak Raina, Lucknow (IN); Arwind Kumar Srivastava, Lucknow (IN); Anil Kumar Rastogi, Lucknow (IN); Puvvada Sri Ramachandra Murthy, Lucknow (IN); Sudhir Srivastava, Lucknow (IN); Onkar Prasad Asthana, Lucknow (IN); Narenda Singh, Lucknow (IN); Nitya Nand, Lucknow (IN)

(73) Assignee: Council of Scientific & Industrial Research (IN)

( * ) Notice: Subject to any disclaimer, the term of this patent is extended or adjusted under 35 U.S.C. 154(b) by 412 days.

(21) Appl. No.: 09/742,424

(22) Filed: Dec. 22, 2000

(65) Prior Publication Data

US 2002/0119206 A1 Aug. 29, 2002

(51) Int. Cl.$^7$ .................. A61K 9/20; A61K 9/48; A61K 9/14; A61K 35/78
(52) U.S. Cl. ............... 424/464; 424/451; 424/489; 424/748
(58) Field of Search .................. 424/464, 451, 424/748, 489, 499

(56) References Cited

U.S. PATENT DOCUMENTS 4,385,053 A * 5/1983 Reisberg et al. ......... 514/424

5,690,948 A 11/1997 McCook et al. ......... 424/401
6,086,889 A 7/2000 Agarwal et al. ......... 424/195.1
6,113,949 A * 9/2000 Brink .................. 424/601
6,436,991 B1 * 8/2002 Majeed et al.

FOREIGN PATENT DOCUMENTS

IN 148265 6/1979

OTHER PUBLICATIONS

Remington's: the Science and Practice of Pharmacy (Mack Publishing Company 1995) pp. 1615–1641.*
Tyrox T–3 Internet Page www.ask4mass.com/thyrox.htm 1996.*
Reilly, Jr. Pharmaceutical Necessities Remington: The Science and Practice of Pharmacy Chapter 80, pp. 1408 & 1414; 199.*
Standaert and Young Goodman and Gilman's the Pharmacological Basis of Therapeutics Ch. 22, pp. 513–514; 1995.*
Dwarakanath, et al., "Research in Some of the Concepts of Ayurveda & The Application of Modern Chemistry & Experimental Pharmacology Therefor", Ayurveda Pradeepika (Ceylon), 1, 69–78 (1970).
Flood, et al., "Memory Enhancing Effects in Male Mice of Pregnenolone and Steroids Metabolically Derived from It", Proc. Natl. Acad. Sci. USA, 89, 1567–1571 (1992). (previously submitted with Information Disclosure Statement filed on Apr. 29, 2002).

(Continued)

Primary Examiner—James M. Spear
Assistant Examiner—Humera N. Sheikh
(74) Attorney, Agent, or Firm—Steven B. Kelber; DLA Piper Rudnick Gray Cary US LLP

(57) ABSTRACT

The present invention provides new uses of Gugulipid, an ethyl acetate extract of the resin of the plant *Comiphora wighitii*, for controlling or preventing cognitive dysfunction, hyperglycemia and some infective conditions of the skin and a method of preparing Gugulipid by agitating the resin in shake flask assembly or sonicating assembly and preparing a solid or a creamy dosage forms.

5 Claims, 3 Drawing Sheets

Cholesterol metabolite and related compounds in *gugulipid*

1
Guggulsterol - I (2)
Guggulsterol - II (3)
Guggulsterol - III (4)

OTHER PUBLICATIONS

Lama, et al., "Development of Tibetan Plant Medicine", Science and Culture, 45, 7, 262–265 (1979).

Gujral, et al., Antiarthritic and Anti–Inflammatory Activity of Gum Guggul (Balsamodendron Mukul Hook), Ind. J. Physiol. Pharmacol., 4, 267–273 (1960).

Nityanand, et al., "Cholesterol Lowering Activity of the Various Fractions of the Guggal", Indian Journal of Experimental Biology, 11, 395–396 (1973).

Tripathi, et al., "Regression of Hyperlipidemia with an Active Principle of Commiphora Mukul", J. Res. Ind. Med., 12, 2, 75, 11–16 (1975), (cited as vol. 10 on p. 3 of the specification).

Bowlby, et al., "Pregnenolone Sulfate Potentiation of N–Methyl–D–Aspartate Receptor Channels in Hippocampal Neurons", Molecular Pharmacology, 43, 813–819 (1993).

Patil, et al., Chemistry of Ayurvedic Crude Drugs –I, Tetrahedron, 28, 2341–2352 (1972).

Hunt, et al., "Oxidative Glycation and Free Radical Production: A Causal Mechanism of Diabetic Complications", Free Radical Res. Commun., 12–13, 115–123 (1991).

Singh, et al., "Guggulsterone, A Potent Hypolipidaemic, Prevents Oxidation of Low Density Lipoprotein", Phytotherapy Research, 11, 291–294 (1997), (cited as vol. II on p. 4 of speceification).

Dev, "Chemistry of Resinous Exudates of Some Indian Trees", Proc. Ind. Natn. Sci. Acad., 49, A, 3, 359–385 (1983).

Brioni, et al., "Drug Effects on Learning and Memory", Chapter F, Vogel, et al. (eds.), Drug Discovery and Evaluation: Pharmacological Assays, Springer–Verlag., Berlin (1997).

* cited by examiner

Figure 1: Cholesterol metabolite and related compounds in *gugulipid*.
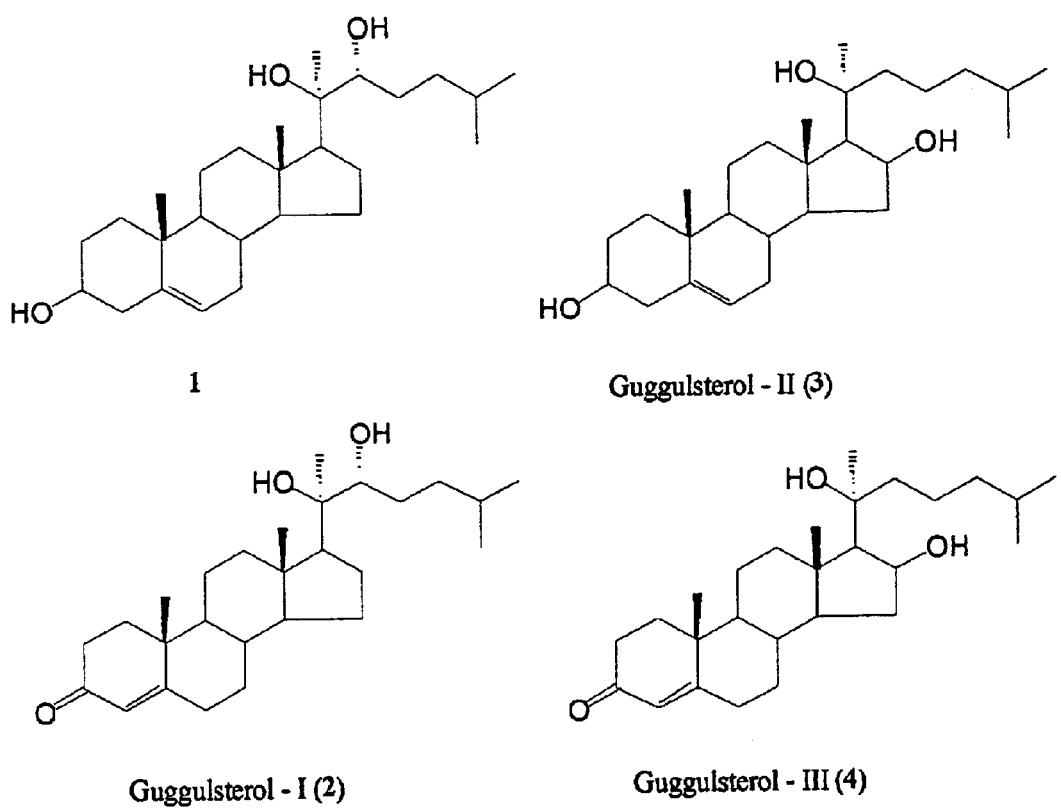

Figure2: Lignans from *Commiphora mukul* and Troglitazone with 1,2- or 1,4-bis-oxygenated phenyl pharmacophore.
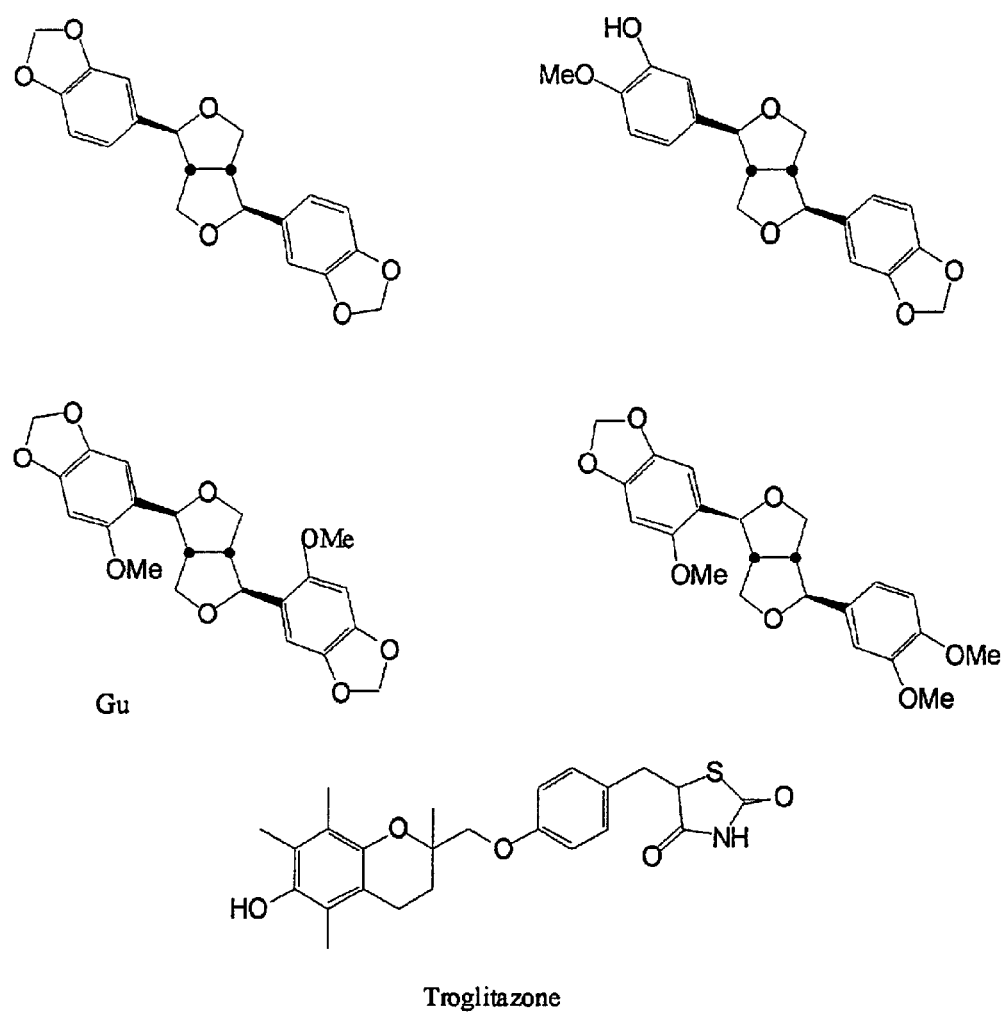

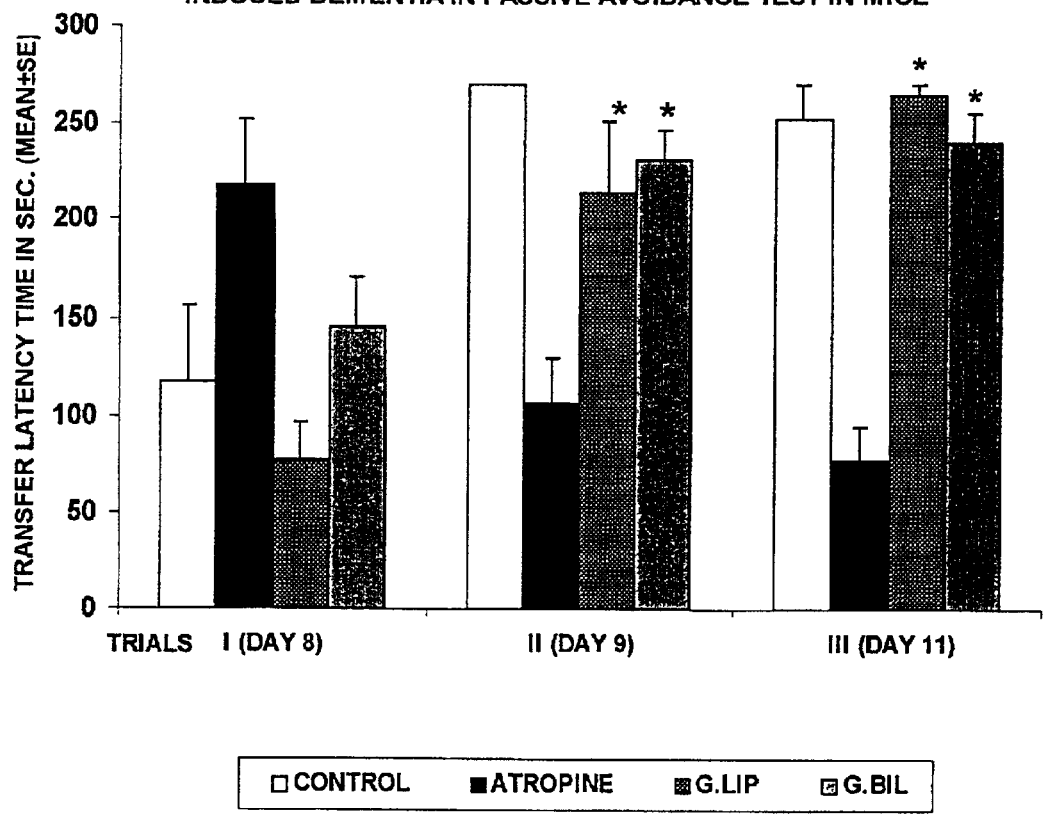

METHOD OF TREATING A COGNITIVE MEMORY DYSFUNCTION USING GUGULIPID

FIELD OF INVENTION

The present invention claims some new uses of Gugulipid, an ethyl acetate extract of the resin of the plant *Comiphora wighitii*, commonly called gum guggulu. These include modifications of the extraction methods and methods for controlling or preventing cognitive dysfunction, hyperglycemia and some infective conditions of the skin.

BACKGROUND OF THE INVENTION

Ayurveda takes a holistic view of human disease. It views any disease as a dysfunction of the whole body rather than of a single organ or physiological process. Most of the Ayurvedic drugs therefore are likely to act on a number of dysfunctions of the body involving a number of organs and functions. Gugulipid, an ethylacetate soluble fraction of gum guggul, was developed as a hypolipidemic agent, based on the reference to the lipid lowering effect of guggul resin in Charak Samhita, a classic text of Ayurveda. Chemopharmacological investigation of this extract resulted in the characterization of guggulsterone [cis-and trans-4, 17 (20)-pregnadiene-3, 16-dione] as the major constituent. Apart from guggulsterone, other chemical constituents in the ethyl acetate soluble fraction added to and modulated the total activity. This fraction rather than pure guggulsterone was developed as a hypolipidemic drug and named gugulipid. As a follow up of the holistic view of Ayurveda of human disease, gugulipid was tested for other related and unrelated conditions/dysfunction and found to possess cognitive and anti-hyperglycemic activities and also improved in general dermal dysfunctions. These novel uses of gugulipid are now claimed.

PRIOR ART

Guggul, highly valued in Indian system of medicine Ayurveda, is the gum resin exudate of a small tree *Commiphora wighitii* belonging to the family Burseraceae. It is specially recommended for the treatment of obesity, lipid disorders and rheumatoid arthritis (Ayurvedic treatise: Sushruta, Vagabhatta). In Tibetan medicine, the plant (*C. Wighitii*) mixed with other herbs is used for skin diseases, anemia, edema, salivation and heaviness of stomach [Lama, S. and Santra, S. C., *Sci. Cult*. 45, 262 (1979)]. Modern pharmacological studies on the crude drug and some of its fractions have supported the claims of Ayurveda. The anti-arthritis and anti-inflammatory activities were confirmed by Gujral and co-workers [Gujral, M. L., Sareen, K., Tangri, K. K., Amma, M. K. P. and Roy, A. K. *Ind. J. Physiol. Pharmacol*. 4, 267 (1960)]. The hypolipidemic and anti-atherosclerotic activities reported by Dwarakanath and Satyawati. [Dwarakanath, C., and Satyawati, G. V. *Ayurveda Pradeepika* (Ceylon), 1, 69 (1970)]; Satyawati, G. V. in "Effect of an indigenous drug and disorders of lipid metabolism with special reference to atherosclerosis and obesity (Medoroga)", M.D. Thesis (Doctor of Ayurvedic Medicine), Banaras Hindu University, Varanasi, (1966)]. Later on, its ethyl acetate extract was developed by joint efforts of Malti-Chem Research Center, Baroda and Central Drug Research Institute, Lucknow as hypolipidemic drug [A process for obtaining hypolipidemic and anti-platelet aggregation fraction from guggul resin. Indian Patent No.148265 dated 6.4.79., N. K. Kapoor., Sukh Dev and S. Nityanand].

A mixed type of mechanism has been implicated for lipid lowering effect of gugulipid. The stimulation of plasma LCAT, hepatic lipases, receptor mediated catabolism of LDL and increased faecal bile acid excretion as well as suppression of hepatic cholesterol biosynthesis are the mechanisms responsible for lipid lowering effect of gugulipid [S. Nityanand and N. K. Kapoor, *Ind J. Exp. Biol*. 11, 395 (1973); N. K. Kapoor and S. Nityanand, *Ind. J. Heart Res. Supp*-1) 22 (1988)]. With the discovery of hypolipidemic activity of the gum resin, systematic chemical investigations were carried out to characterize compounds of the gum resin responsible for hypolipidemic activity. Mc Cook et al. have recently claimed alcoholic extract of gum guggul for controlling or preventing sebum secretion from sebocytes which is associated with a shiny, undesirable appearance and a disagreeable tactile sensation [J. P. Mc Cook et. al. U.S. Pat. No. 5,690,948 (1997). Antisebum and antioxidant compositions containing gugulipid and alcoholic fractions thereof]. The applicants have earlier obtained a U.S. Pat. No. 6,086, 889 for a process for isolation of lipid fraction containing Z and E guggulsterones from the aerial parts of the plant *Comiphora wightii*. The said process comprises the steps of soaking or soxhlet extracting the powdered aerial part of the plant with a non polar solvent; filtering or decanting the extract; soaking the material again in polar solvent; filtering and concentrating the extracted material in the polar solvent under reduced pressure and gel filtration or silica gel chromatography to obtain Z and E ketosteroid containing lipid fraction. The present invention introduces non-obvious modifications to the extraction method as described in the earlier prior art and describes new uses of the Gugulipid, which were not known earlier.

GENESIS OF THE INVENTION

With the isolation of variety of compounds of varied structural classes such as lignans, lipids, diterpenoids and steroids, we initiated quite early a program to investigate structure based biological profiles of gugulipid. Earlier, it was revealed that the hypolipidemic and thyroid stimulating actions of guggulsterone [Tripathi, S. N., Gupta, M. Dwivedi, L. D. and Sen, S. P., *J. Res. Ind. Med*. 10, 11 (1975); Singh, V. and Kapoor, N. K. in "Stimulation of low density lipoprotein receptors activity in liver membrane of guggulsterone treated rats." In Proceedings of Society of Biological Chemists, India, 57th Annual Meeting, CSIR Center for Biochemicals, New Delhi, Oct. 9-12, 1988].

ROLE IN IMPROVING COGNITIVE FUNCTIONS

Recent developments in understanding of neurosteroids, role of free radicals and antioxidants in brain function as well as in hyperglycemia prompted us to explore gugulipid for these activities. Behavioral studies have suggested a potential role of pregnenolone, in particular, for memory enhancement. Intracerebroventricular (i.c.v.) administration of pregnenolone and pregnenolone sulfate leads to an amelioration in various memory task in rodents [Flood, J. F., Morley, J. F., and Robert, E., Memory enhancing effects in male mice of pregnenolone and of steroids metabolically derived from it; *Proc. Natl. Acad Sci*. USA; 89, 1567 (1992)]. These memory-enhancing effects might be attributed to the N-methyl-D-aspartate (NMDA)-antagonistic properties of pregnenolone sulfate since NMDA agonists have been shown to impair cognitive functions in rodents [Bowlby, M. R., Pregnenolone sulfate potentiation of N-methyl-D-aspartate receptor channels in hippocampal neurons. *Mol. Pharmacol.*, 43, 813 (1993)]. As already stated, cholesterol is the precursor of neurosteroid pregnenolone. These findings prompted us to explore memory enhancing properties of gugulipid because of similarity among biogenic precursor of pregnenolone (1) and steroids present in Gugulipid such as guggulsterol-I (2), guggulsterol-II (3) and guggulsterol-III (4) (FIG. 1) [V. D. Patil, U. R. Nayak and Sukh Dev: Chemistry of Ayurvedic Crude Drugs-I, *Tetrahedron* 28, 2341 (1972)].

ROLE IN IMPROVEMENT OF DIABETIC CONDITION

Recent years have seen increasing interest in the role of free radical oxidative damage in human disease. Free radicals are highly reactive species that have the potential to oxidize biological molecules including proteins, lipids and DNA. To prevent or retard oxidation, rich arrays of natural antioxidant mechanism exist. These antioxidant defense mechanisms have been found defective in many diseases. Increased production of free radicals has been strongly implicated in the pathophysiology of diabetes and atherosclerosis. Glucose combines with serum proteins and lipoproteins in a non-enzymatic glycation reaction and may auto-oxidize in situ generating free radicals and causing local oxidative damage [Hunt, J. V., Wolff, S. P. in "Oxidative glycation and free radical production; a causal mechanism of diabetic complications". *Free Radical. Res. Commun.* 12-13,115 (1991)]. The free radical scavenging antioxidants react preferentially with free radicals before vital structure can be attacked.

Troglitazone, a hypoglycemic agent has been shown to exhibit strong antioxidant activity. Its 1,4-bis-oxygenated phenyl pattern of chroman skeleton is real pharmacophore responsible for antioxidant property. Gugulipid and gugguisterone are also known to have antioxidant property [Guggulsterone, a potent hypolipidemic, prevents oxidation of low density lipoproteins, K. Singh, R. Chander and N. K. Kapoor, *Phytotherapy Research, II*, 291 (1997)]. There are several molecules in lignan class where 1,2-or 1,4-bis-oxygenated phenyl pharmacophoric pattern are present (FIG. 2). [Sukh Dev, *Proc. Ind. Sci. Acad.* 49A, 359 (1983)].

Thus the presence of above biologically potential class of molecules makes gugulipid a good candidate for exploration against diseases associated with dyslipidemia, hyperglycemia and behavior.

OBJECTS OF THE PRESENT INVENTION

An object of the present invention was to develop a method of extraction of Guggul resin by continuous shaking or sonication procedure to obtain improved yields of the extract. Another object of the present invention was to develop cognition enhancing effect of gugulipid orally in any pharmaceutical preparations.

Still another object of the present invention was to develop a method of reducing, preventing or controlling hyperglycemic conditions by consuming gugulipid in any pharmaceutically acceptable formulations.

Another object of the invention is to develop a method of improving conditions of infected skin.

SUMMARY OF THE INVENTION

The present provides process for extraction gugulipid of resin from aerial branches of the plant *C. wighitii* comprises suspending gum/resin with a non-polar solvent, filtration or decantation, repetition of the process for extraction of fatty acids, extraction of residual matter with ethyl acetate by continuous shaking or sonication procedure, mixing of polar and nonpolar fractions and filtration to remove solid suspension and finally the solvent is removed to get gugulipid.

The invention also provides method for the preparation of pharmaceutically acceptable compositions for controlling hyperglycemic conditions and improving conditions of infected skin.

DETAILED DESCRIPTION OF THE INVENTION

Accordingly, the present invention provides process for extraction gugulipid of resin from aerial branches of the plant *C. wighitii*, said process comprising a) suspending gum/resin of plant *C. wighitti* in a non-polar solvent for a period of 5 to 8 hours, b) filtration or decantation of the soluble portion, c) repeating the above steps for the extraction of fatty matter, d) extraction of residual matter with ethyl acetate by agitation on shake flask or sonicating assembly.

e) mixing the extracts from steps (a), (c) and (d) and filtering to remove solid suspension, to obtain gugulipid, and if desired, f) converting the gugulipid into solid or creamy dosage forms by any known method.

The term Gugulipid as used herein means an ethyl acetate extract of gum/resin Guggul from the tree *C. wighti*.

The term "Ethyl acetate extract" means the non-aqueous fraction of gum/resin.

In an embodiment, the non-polar solvent is selected from n-hexane, cyclohexane or any other solvents.

In another embodiment of the invention, the yield of Gugulipid from the said process is in between 45–60%.

In another embodiment of the invention, the solid dosage form is obtained by maceration of the component gugulipid, starch and microcrystalline cellulose in suitable proportions in a mixer till the mixture becomes flowable powder.

In another embodiment of the invention, the cream formulations is obtained by dissolving gugulipid alone or with help of solvent in suitable portions of polyethylene glycol by heating on water-bath and pulling off the solvent.

In another embodiment of the invention, gugulipid in combination with or associated with an additive is used for controlling or preventing cognitive dysfunction, hyperglycemia and some infective conditions of the skin in mammals.

In another embodiment of the invention, Gugulipid is administered in the form of extracts, solid dosages or cream formulations as may be suitable.

In another embodiment of the invention, for enhancing cognitional behavior by feeding gugulipid or mixed with other agent of similar property given orally in the form of suitable pharmaceutical preparations and with amount necessary for activity.

In another embodiment of the invention, for reversal of Atropine induced amnesia in male swiss mice by administrating gugulipid dosage equivalent to 40 mg/kg/day for about 7 days either in the form of extracts or solid dosage.

In another embodiment of the invention, Gugulipid is used for treatment of patients suffering from human memory dysfunctions like Alzheimers disease and Korsakoff's disease alone or in combination with other treatments.

In another embodiment of the invention, gugulipid in combination with or associated with an additive is used for reducing, preventing or controlling hyperglycemic conditions by consuming necessary amount of gugulipid for activity in any pharmaceutically acceptable formulations.

In yet another embodiment gugulipid as a hypoglycemic agent decrease the blood glucose level by 30–60% of streptozotocin induced diabetic rats at 100 mg/kg body weight between 1–7 hrs and evident from first hour post administration of gugulipid either in extract or solid dosage form.

In yet another embodiment Gugulipid has hypoglycemic effect at 100 mg/kg of body weight per dose and the average lowering of about 45% in blood glucose profile between 3–7 hrs.

In yet another embodiment, Gugulipid has hypoglycemic effect at 100 mg/kg of body weight dose in glucose-loaded rats and the peak lowering effect is between 30–60 min. post glucose-load.

The inventive methods of controlling memory dysfunction, hyperglycemic or infectious conditions of skin conditions employ gugulipid or extract of gum/resin in pharmaceutically acceptable dosage forms.

BRIEF DESCRIPTION OF ACCOMPANYING DRAWINGS

FIG. 1 shows the structure of Cholesterol metabolite and related compounds in gugulipid.

FIG. 2 shows the structure of Lignans from *Commiphora mukul* and Troglitazone with 1,2- or 1,4-bis-oxygenated phenyl pharmacophore.

FIG. 3 shows the effect of Gugulipid and Ginkobyloba on Atropine induced dementia in passive avoidance test.

The following examples are given by the way of illustration and should not be construed to limit the scope of the present invention.

EXAMPLE-I

This example discloses the method of obtaining gugulipid in higher yields and preparation of its dosages formulations.
Improved Extraction Procedure of Gugulipid From Resin:

In earlier extractive procedure, the occasional hand shaking of gum/resin produced gugulipid in 30–40% yields. When above hand shaking procedure is changed to shaking the content in continuous shake flask assembly driven by electric motor or to agitation with sonicator, it improved the yields of gugulipid appreciably.

In a typical procedure: gum/resin (200 g) is suspended in n-hexane (~200 ml) in shake flask assembly for 5–6 hrs. Hexane soluble portion is decanted off and procedure is repeated once again to extract fatty matters. The residual material changes from sticky to freely movable matter which is then extracted with ethyl acetate (~3×200 ml) by shaking on continuous shake-flask assembly for 10–12 h. Both the hexane and ethyl acetate fractions are mixed and filtered to remove solid suspension. The solvent removed to give gugulipid (96 g, 45% yield). The various experiments revealed the improvement of the total yield to the extent of 45–50%.

The similar experiment in sonicating assembly (~30 min, 5000 Hz) also exhibits the improvement in yield of about 45 to 65%.

The gugulipid conforms to the specifications of Indian Pharmacopoeia, 1996.

The solid dosage form may be obtained by maceration of the component gugulipid, starch and microcrystalline cellulose in suitable proportions in a mixer till the mixture becomes flowable powder. This can be filled in capsules or converted into tablets as per desired specifications.

In a typical example, gugulipid (40 g) was dissolved in ethyl alcohol (~100 ml). To this solution, starch (5.5 g) and microcrystalline cellulose (54.5 g) were added and mixed well. The solvent was evaporated below 50° C. and the material was passed through 40-mesh size sieve to obtain granules. The granules were then compressed into tablets.

The cream formulations may be obtained by dissolving gugulipid alone or with help of solvent in suitable portions of polyethylene glycol PEG 400, PEG 1500 and PEG 6000 by heating on water-bath and pulling off the solvent.

In a typical example, gugulipid (log) was dissolved in PEG 400(52 g), to this PEG 1500 (112 g) and PEG 6000 (26 g) was added, heated on water bath till all the contents melt completely. The solution was cooled with occasional stirring.

The following specific examples further illustrate the invention, but the invention is not limited thereto.

EXAMPLE II

This example reports cognition enhancing property of gugulipid in animal model of Alzheimer's disease.
Comparative Study of Gugulipid and Ginkgo Biloba as Cognitive Enhancer by Passive Avoidance Test.

One of the most common tests in memory research is the inhibition to imitate activities or learned habits. The term "passive avoidance" is usually employed to describe experiments in which the animal learns to avoid a noxious event by suppressing a particular behavior. Different forms of human memory dysfunctions can be modeled in the animal by the administration of different centrally acting drugs to normal, healthy subjects. Anticholinergics like scopolamine or atropine produces transient amnestic effects similar to the deficits observed in the patients with Alzheimer's disease (AD), whereas benzodiazepines produce effects similar to the anterograde amnesia typical of patients with Korsakoff's disease (KD).
Rationale of Test Procedure:

When a mouse or rat is put in a closed chamber consisting of interconnected dark and lighted compartments, it prefers to be in dark near walls, but when given an electric shock in the dark compartment it moves to the lighted compartment and remains there till it remembers the danger. A typical paradigm of testing cognition behavior consist of three phases: Familiarization: the animal is placed in the lighted compartment and after 10 seconds of exploration, it returns to the home cage. Learning: Immediately after the animal has come to the dark room, an unavoidable foot shock is applied and the animals returned to the illuminated side. Retention test: 24 hr after the learning trial, the animal is again placed to the illuminated side after feeding test drug and the procedure of learning is repeated. The latency period is measured. Evaluation: the time of latency during the learning and retention test phase is measured. A prolongation of the latency period is defined as learning.
Passive Avoidance Test The mice were subjected to single trial passive avoidance test as described by Brioni et al [Brioni, J. D.; Hock, F. J. and McGaugh, J. J. in 'Drug Effects on Learning and Memory'. H. G. Vogel and W. H. Vogel (Eds.). *Drug Discovery and Evaluation: Pharmacological Assays*" Springer-Verlag. Berlin, 1997]. The passive avoidance test was studied by a computerized shuttle box (Columbus Instruments, Ohio, USA) provided with a software program PACS 30. The shuttle box is comprised of two compartments. An automated door was used to isolate the compartments. After an exploration period of 30 seconds for acclimatization, the animal was subjected to a trial of 270 seconds. Each mouse was placed in the bright (light intensity 10) compartment and on transfer into the dark compartment it was given an electric shock (0.5 mA for 5 s) through a floor grid. The computerized door was set to close upon transfer, subjecting the mouse to the full duration of electric shock. Infrared sensors monitor the transfer from one compartment to another, which recorded as transfer latency time (TLT) in seconds. TLT was recorded in control and acute stress group (30 min after immobilization) on day 1 (trial I) and next day (trial II). In chronic stress group trial I was given 30 min after immobilization (day 5) and trial II 24 hrs later. The criterion for improved cognitive activity was taken as an increase in the TLT on trial II as compared to trial I.

Procedure

Effect of Administration of Gugulipid as Extract

Male Swiss mice (25–30 g) were randomized into 4 groups (n=10). Extracts Gugulipid (40 mg/kg/day.) and $G.$ $biloba$ (30 mg/kg/day.) were administered in one group each for 7 days, in the other two groups corresponding volume vehicle was administered. On the $8^{th}$ day atropine (4 mg/kg, imp.) was administered in each animal of extract treated and one vehicle group 5 min before Passive Avoidance Test in a computerized shuttle box using PACS-30 software. The transfer latency time (TLT) from illuminated chamber to the dark chamber was recorded in all the groups. Mean values and standard error (SE) of mean was calculated TLT (passive avoidance test) of each group. The significance of difference between the values of two groups was determined by Student's 't' test. Gugulipid is equally active to the standard drug $G.$ $biloba$ and the data is presented in bar diagram (FIG. 3). The experiments were carried out according to the following protocol:

PLANT EXTRACT (40 mg/kg,.p.o., daily for 7 days, swiss mice 25–30 g)

↓

$8^{th}$ day

PASSIVE AVOIDANCE TEST

Parameter: Transfer Latency Time

Anticholinergic: Atropine (5 min prior to test)

↓

TRIAL (I)

$8^{th}$ dose of extract immediately after trial

↓

TRIAL (II)

$9^{th}$ dose of extract immediately after trial

↓

$10^{th}$ day

NO TRIAL $10^{th}$ dose of extract

↓

$11^{th}$ day

TRIAL (III)

↑Latency time, >80% no transfer response

EFFECTIVE

Both the extract treated groups showed significant reversal of atropine induced amnesia.

Effect of Administration of Solid Dosage of Gugulipid:

Gugulipid solid dosage form equivalent to 40 mg/kg/day for 7 days was administered in swiss mice. It was found equally effective to the standard drug Ginkobiloba in passive avoidance test model. Solid dosage form was prepared by mixing gugulipid with starch or microcrystalline cellulose.

Example III

This example reports anti-hyperglycemic property of gugulipid in streptozotocin induced diabetic rats.

Anti-hyperglycemic Activity in Streptozotocin Induced Diabetic Rats:

Charles Foster strain male albino rats of the body weight 140±20. 0 g were used in this experiment. Streptozotocin was dissolved in citrate buffer and calculated amount of the fresh solution was injected in over night starved rats (50 mg/kg body weight, intraperitoneal, i.p.). Blood samples were collected 48 hrs after the streptozotocin administration. Rats having glucose levels 250 mg/dl in blood were finally selected for the experiments. They were divided in two groups of six rats each. Animals of group I received an equal amount of methylcellulose, while animals of group II received gugulipid (1.2% in methylcellulose) 100 mg/kg body weight respectively. Blood samples were collected at 0 hour and after that at hourly intervals up to 7 hrs. Post administration of vehicle/gugulipid and blood glucose level was immediately estimated by glucose oxidase method. Food but not water was with held during the experiment.

Glucose Estimation:

Glucose is oxidized by glucose oxidase to gluconic acid. The dihydrogen peroxide produced in the reaction is determined by means of o-dianisidine in the presence of peroxidase yielding a colored dye. The amount of dye formed is the measure of the glucose concentration in the sample. Absorption of oxidized o-dianisidine can be measured at 436 nm.

TABLE 1

$$\% \text{ Anti-hyperglycemic activity} = \frac{\text{Average blood glucose level of test substance-treated group at test time}}{\text{Average blood glucose level of untreated group at that time}} \times 100$$

Blood glucose profile of streptozotocin induced diabetic rats post administration of gugulipid (single dose).

| Group | Blood glucose level (mg/dl) hours post treatment | | | | | | | |
|---|---|---|---|---|---|---|---|---|
| | 0 | 1 | 2 | 3 | 4 | 5 | 6 | 7 |
| Control | 312 ± 18.5 | 320 ± 17.4 | 310 ± 14.3 | 311 ± 15.9 | 309 ± 15.8 | 305 ± 15.5 | 305 ± 20.0 | 306 ± 19.5 |
| Gugulipid | 293$^{Ns}$ ± 13.3 | 222* ± 27.9 (−30.6) | 222* ± 27.9 (−30.9) | 186** ± 35.8 (−40.19) | 171** ± 29.4 (−44.66) | 156** ± 36.3 (−48.85) | 139*** ± 22.9 (−54.42) | 107*** ± 18.4 (−65.03) |

Figure in parenthesis shows % lowering in blood-glucose level from control value
$^{Ns}$not significant;
*significant ($p < 0.05$);
**highly significant ($p < 0.01$);
***Very highly significant ($p < 0.001$).

Conclusion:

The results shown in table-1 clearly demonstrates that Gugulipid has hypoglycemic effect at 100 mg/kg body weight dose and the average lowering was observed 45% between 3 to 7 h. in blood glucose profile, was evident from first hour post administration of gugulipid.

Anti-hyperglycemic Activity of Gugulipid when Administered as Solid Dosage:

Tests were carried out on Charles foster albino rats in streptozotocin induced diabetic model. Gugulipid in solid dosage form equivalent to 100 mg/kg caused about 45% reduction in glucose level between 3 to 7 hours after dose administration.

Anti-hyperglycemic Activity of Gugulipid in Glucose Loaded Rats:

Charles foster male albino rats as obtained from the animal colony of the Institute were housed in plastic cages. Their blood glucose profiles were determined after starving the animals over night. Animals showing blood glucose profile between 60 to 70 mg/dl were finally selected, and divided into two groups consisting of five animals in each group. Animals of group II received gugulipid suspension in 1.2% methylcellulose) at a dose level of 100 mg/kg body weight orally whereas the animals of group-I received an equivalent amount of vehicle. A glucose load of 2.0 g/kg was given to each of the animal's 30 minutes post treatment. Blood was collected at 30, 60, 90, and 120 minutes post glucose load and analyzed for blood glucose. Percent inhibition of the test substance was determined according to the following formula:

TABLE 2

$$\% \text{ Anti-hyperglycemic activity} = 100 - \frac{\text{Average blood glucose level of test substance-treated group at test time}}{\text{Average blood glucose level of untreated group at that time}} \times 100$$

Blood glucose level profile of glucose loaded rats.

| Group | Blood glucose level (mg/dl) hours post treatment | | | | |
|---|---|---|---|---|---|
| | 0 min | 30 min | 60 min | 90 min | 120 min |
| Control | 67.75 ± 2.7 | 105.0 ± 1.98 | 92.87 ± 3.0 | 79.43 ± 1.48 | 75.57 ± 2.6 |
| Gugulipid (100 mg/kg) | 64.85$^{Ns}$ ± 2.3 | 73.14*** ± 2.1 (−30.34) | 74.82** ± 2.9 (−19.43) | 82.23 ± 2.3 | 79.3 ± 3.0 |

Figure in parenthesis shows % lowering in blood-glucose level from control value.
$^{Ns}$not significant ($p > 0.05$),
**Highly significant ($p < 0.01$),
***Very highly significant ($p < 0.0$)

The results shown in table 2 clearly demonstrates that gugulipid has hypoglycemic effect at 100 mg/kg body weight dose and the peak lowering effect was observed between 30 to 60 minutes post-glucose load.

Conclusion

Gugulipid has marked hypoglycemic effect at 100 mg/kg body weight dose in glucose-loaded rats.

Example-IV

This example reports Antifungal property of gugulipid for dermal conditions.

Antifungal Property of gugulipid:

Considering its use in skin diseases in Ayurveda, the present study was carried out with gugulipid for some of the common fungal skin conditions. As there was no knowledge about the skin diseases where gugulipid ointment can be useful, a search—screening clinical trial was under taken on variety of skin diseases. The ointment was prepared by dissolving gugulipid with the help of solvent in a suitable proposition of polyethylene glycol (PEG) 400, PEG-1500.and PEG-6000 by heating on water bath and pulling off the solvent. The placebo sample was prepared by mixing PEGs in above ratios. Each patient first applied the placebo-cream twice a day for a week and then shifted to gugulipid cream. 5% content of Gugulipid cream in PEG applied twice a day on human skin was effective in chronic dermatitis, ring worm and itching due to the lesions due to the infestation of fungi (such as *Candida albicans, Taenia cruris, Taenia pedis*), allergic conditions skin and had anti-inflammatory activity associated with these infective conditions.

It should be understood that the specific forms of the invention illustrated and described so far are intended to be representative only. The change, including but not limited to those suggested in this specification, may be made in the illustrated embodiments without departing from the clear teaching of the disclosure. Accordingly, reference should be made to the following appended claims in determining the full scope of the invention.

Advantages of the Present Invention:

1. The extraction of Guggul resin by continuous shaking or sonification procedure as described in the present invention exhibits improvement in yields as compared to the conventional method of extraction.
2. The present invention also provides a method for preparing solid dosage and cream formulations of Gugulipid in addition to extracts. Gugulipid can therefore be provided in form of extracts, tablets or cream formulations whichever is more suitable for the treatment of a particular ailment.
3. The present invention provides new uses of Gugulipid for enhancement of cognition, reducing, controlling or preventing hyperglycemic conditions and improving infectious condition of the skin.

What is claimed is:

1. A method of treating a cognitive memory dysfunction in a mammal, said method comprising administering to said mammal a pharmaceutically acceptable composition consisting essentially of a capsule or a tablet of a memory enhancing effective amount of gugulipid, starch, microcrystalline cellulose at a yield of 45–60%, wherein said gugulipid is administered at a dosage level equivalent to 40 mglkgldav for 7 days.

2. The method of claim 1, wherein the tablet is obtained by dissolving gugulipid with ethanol solvent and adding starch and microcrystalline cellulose, evaporating the solvent, passing the material through 40 mesh size sieve to get the granules and compressing the granules to obtain tablets.

3. The method of claim 1, wherein the gugulipid is used for treating patients suffering from human memory dysfunctions caused by Alzheimer's disease or Korsakoff's disease.

4. The method of claim 1, wherein said dysfunction is an anticholinergic-induced amnesia.

5. The method of claim 4, wherein the gugulipid is administered as extract or solid dosage.

* * * * *